(12) United States Patent
Cohen (10) Patent No.: US 10,143,825 B2
(45) Date of Patent: Dec. 4, 2018

(54) CATHETER MANAGEMENT SYSTEM

(71) Applicant: Todd J. Cohen, Port Washington, NY (US)

(72) Inventor: Todd J. Cohen, Port Washington, NY (US)

(73) Assignee: Nexus Control Systems, LLC, Port Washington, DC (US)

( * ) Notice: Subject to any disclaimer, the term of this patent is extended or adjusted under 35 U.S.C. 154(b) by 0 days.

(21) Appl. No.: 14/215,333

(22) Filed: Mar. 17, 2014

(65) Prior Publication Data

US 2014/0276441 A1 Sep. 18, 2014

Related U.S. Application Data

(60) Provisional application No. 61/787,391, filed on Mar. 15, 2013.

(51) Int. Cl.
*A61M 25/02* (2006.01)

(52) U.S. Cl.
CPC ..... *A61M 25/02* (2013.01); *A61M 2025/0253* (2013.01); *A61M 2025/0273* (2013.01)

(58) Field of Classification Search
CPC ............... A61M 25/02; A61M 25/002; A61M 2025/0246; A61M 2025/0253; A61M 2025/026; A61M 2025/0266; A61M 2025/0273; A61M 3/027; A61M 2025/213; A61M 2025/0206
See application file for complete search history.

(56) References Cited

U.S. PATENT DOCUMENTS

| | | | |
|---|---|---|---|
| 3,696,920 A | 10/1972 | Lahay | |
| 4,583,976 A | 4/1986 | Ferguson | |
| 5,643,217 A * | 7/1997 | Dobkin | 604/180 |
| 6,382,568 B1 | 5/2002 | Snell | |
| 2003/0132352 A1 | 7/2003 | Weaver | |
| 2008/0221526 A1* | 9/2008 | Fleischer | 604/180 |
| 2010/0006738 A1 | 1/2010 | Teirstein | |
| 2010/0010475 A1* | 1/2010 | Teirstein et al. | 604/528 |
| 2001/0248125 | 10/2011 | D'Andria | |

FOREIGN PATENT DOCUMENTS

| | | |
|---|---|---|
| EP | 0720836 A2 | 1/1996 |
| WO | 2005051472 A2 | 6/2005 |
| WO | 2012062717 A1 | 4/2012 |

* cited by examiner

*Primary Examiner* — Bradley J Osinski
*Assistant Examiner* — Nilay Shah
(74) *Attorney, Agent, or Firm* — William Dippert; Laurence Greenberg; Werner Stemer (57) ABSTRACT

A catheter management system comprises several layers where a top layer has one or more channels to receive one or more elongated medical devices or members and a bottom layer comprises adhesive to secure the catheter management system to a patient or other secure site in the operating field. A firm upper surface causes the elongated medical devices or members to stay in the channels, whereas a firm inner layer facilitates maintaining the shape of the catheter management system and providing resistance for an operator to easily release an elongated medical device or member.

12 Claims, 3 Drawing Sheets

CATHETER MANAGEMENT SYSTEM

This application is based upon and claims the benefit of the filing date of commonly assigned U.S. Provisional Patent Application Ser. No. 61/787,391, filed Mar. 15, 2013, incorporated herein by reference in its entirety.

FIELD OF THE INVENTION

This patent application is directed to a catheter management system. More particularly, this patent application is directed to a catheter management system comprising a flexible substrate having at least two layers and one or more lateral grooves, slots, slits, or openings to receive and release elongated medical devices or members such as catheters, guide wires, leads, sheaths, and the like, used for surgical or intravascular medical procedures. The catheter management system's primary function is to be attached near or on a patient to hold a variety of elongated medical devices or members in position and easily release said elongated medical devices or members for repositioning and/or removal.

BACKGROUND OF THE INVENTION

When procedures are performed on a patient in a catheterization lab, an electrophysiology laboratory, or an interventional radiology or operative suite, a number of longitudinally extending, or elongated, medical devices or members are employed. Dependent upon which procedure is being performed, any number of catheters, guide wires, guiding catheters, sheaths, leads, or other elongated medical devices or members can be used. These elongated medical devices or members are primarily very long thin tubes or rods that may come in a variety of lengths and widths. The operator has the responsibility to carefully manipulate these elongated medical devices or members in sometimes very complex proceedings.

In some of the procedures it is necessary to insert one elongated medical device or member into a patient and then to keep that elongated medical device or member in position while an operator inserts or retracts another elongated medical device or member. As a result, there can be a number of coextensively extending elongated medical devices or members where the relative positions have to be maintained. At the present time, it is part of the operator's technique to maintain the respective elongated medical devices or members in desired relationships to one another.

The management of coextensively extending elongated medical devices or members is a concern during, for example, an electrophysiology study or a catheter ablation procedure. Typically a number of catheters are placed through either veins or arteries into a variety of locations within the heart. These catheters can, for example, record specific potentials, and they often move out of place. This movement is due to the fact that standard introducer sheaths only provide a small amount of resistance and patient and/or catheter movement during the procedure can easily dislodge a catheter tip's position. Also, a patient may move his or her body or legs when shocked or due to discomfort. Sometimes a more bulky and expensive "lock-down" sheath can be used to prevent catheter movement; however, this is impractical for use in procedures that require multiple catheters. Having to reposition catheters or wires adds time to a procedure and increases radiation exposure.

At times an operator must deliver and keep a flexible elongated medical device or member in a fixed position either through a single vessel or through vessels which terminate in a single vascular structure. In one circumstance, the operator passes two or more pairs of flexible elongated medical devices or members through the same blood vessel, either directly via a cut-down procedure, though as single introducer, or through a Y-adaptor. The multiple flexible elongated medical devices or members travel down a single or multiple veins and/or arteries such that the elongated medical devices or members are positioned in the heart and circulatory either for diagnostic and/or therapeutic purposes. Their apposition, next to each other, may hinder the stable position of one member, while the other is positioned.

The multiple elongated medical devices or members may be, for example, guide wires, catheters, pacemaker leads, or sheaths. Since the elongated medical devices or members may have similar points of entry such as the right groin for the right femoral artery and vein, the operator must take steps to keep the elongated medical devices or members organized and separate from each other, and to keep each member identified with the location and purpose. It is important to keep the elongated medical devices or members separate for several reasons. If the elongated medical devices or members become twisted, they will interact with one another. For instance, when the operator moves one wire or catheter, another wire or catheter may also move out of position. Further, different devices, such as stents, are typically passed over the guide wires on the catheters; therefore, if the wire/catheter pairs become twisted with each other, accurate advancement of the associated devices is hindered. Also, since different devices are passed over the different wires on the catheters, the operator must take steps to identify each wire so as not to confuse which wire is going down which vessel or branch vessel.

During electrophysiology procedures and/or cardiac catheter ablation procedures multiple catheters are positioned in a single blood vessel such as the right femoral vein and perhaps the right femoral artery, all in proximity to one another. The wires are often placed in very discrete locations to record and diagnose a particular condition. It is not infrequent for four such catheters to be located in one groin location. Movement of the patient could result in catheter movement and require repositioning. Lock-down introducers are useful, but expensive. There is a need for a simple and inexpensive catheter management system to hold catheters of a variety of shapes in place and for such a system to be able to rapidly and quickly release the catheter(s) for further mapping and repositioning.

Another comparable example of the same effect as described above is implantation of a multi-lead implantable heart rhythm device such as a pacemaker or defibrillator (and a biventricular device typically has three leads). Very frequently, those leads are implanted through a single blood vessel such as the cephalic, auxillary, or subclavian vein. To prevent the problem of unintended movement, the operator may have to percutaneously stick a second blood vessel, thereby subjecting the patient to additional vascular or pneumothorax risk. In addition, placement of "a third lead" such as the left ventricular lead used in biventricular devices, eventually requires a process of slitting a long sheath, which often may dislodge previously placed leads in more traditional locations such as the right atrium and ventricle. This typically lengthens and complicates these procedures. A method of easily securing leads while positioning another is needed. In addition, a method of securing leads while slitting a deliverable lead is also required. Further, a method of easily releasing the leads for additional positioning is required.

OBJECTS OF THE INVENTION

It is an object of the invention to provide a simple and effective catheter management system.

It is also an object of the invention to provide a catheter management system comprised of a flexible substrate wherein an elongated medical device or member such as a catheter, wire, sheath, or lead is positioned in a catheterization lab or a surgical field to maintain the relative positions of the elongated medical devices or members.

It is a further object of the invention to provide a catheter management system comprising a flexible substrate comprising at least two layers and at least one lateral groove, slot, slit, or opening.

It is a yet further object of the invention to provide a catheter management system comprising a flexible substrate comprising at least three layers and at least one or more lateral grooves, slots, slits, or openings.

It is a yet further object of the invention to provide an alternative base to the bottom or lower surface of the catheter management system to adhere to a sterile field during a procedure.

It is a yet further object to provide printed material on the top surface of the catheter management system to instruct, warn, market, promote, and/or advertise.

It is a yet further object to provide a device to free up an operator's hand to perform other functions or tasks without losing progress made in positioning a catheter, wire, sheath, lead, or other elongated medical device or member.

It is a yet further object to provide a device to allow an operator to grab and manipulate a catheter, sheath, wire, lead, or other elongated medical device or member without having to take multiple steps to release a catheter, sheath, wire, lead, or other elongated medical device or member from a securing device.

It is a yet further object to provide comfort to an operator's hand during a procedure by allowing the operator to use less finger strength to maneuver a catheter, sheath, wire, lead, or other elongated medical device or member than would normally be required.

These and other objects of the invention will become more apparent from the discussion below.

SUMMARY OF THE INVENTION

The catheter management system described below is a simple, inexpensive, and useful tool which, because of its design, can easily hold and release a variety of catheters, guide wires, implantable leads, sheaths, and other elongated medical devices or members. To provide this functionality, a simple disposable medical device having an adhesive component has been developed to hold a variety of elongated medical devices or members of different sizes in place, organize their purpose, and provide for easy release during repositioning and/or removal. A multi-firmness design, for example, a top layer may be stiffer or more rigid than the adjacent lower layer, helps hold a catheter or other elongated medical device or member in place while preventing rotation or other movement.

A catheter management system (CMS) has been designed to assist an operator in a catheterization lab, although the catheter management system could be useful in other hospital or operating situations, such as an operating room, an electrophysiology laboratory, or an interventional radiology suite. The catheter management system comprises a pliable or flexible substrate or pad having at least one lateral groove, slot, slit, gap, or opening, that is, a channel, capable of holding a catheter, guide wire, lead, sheath, or other elongated medical device or member of various shapes and sizes. The channel opens upon downward pressure on a catheter, guide wire, lead, sheath, or other elongated medical device or member to close or form around the catheter, guide wire, lead, sheath, or other elongated medical device or member. The catheter, guide wire, lead, sheath, or other elongated medical device or member is held in the channel until the operator gently urges the catheter, guide wire, lead, sheath, or other elongated medical device or member upward to release it from the channel. In one embodiment of the invention, a channel opens upon simultaneous downward pressure at two points on the upper surface about a half an inch or so adjacent to the channel.

In one embodiment of the invention, the catheter management system essentially comprises two layers or components, a first layer or component, preferably with varying firmness, to receive one or more catheters, guide wires, leads, sheaths, or other elongated medical devices or members and a second layer or component having an adhesive backing or surface to affix or attach the catheter management system to a suitable surface, such as the patient's skin, a sterile drape, an operating table, or a gurney. It is within the scope of the invention that there could be one or more additional layers, such as an upper, slightly rigid layer atop the first layer or a slightly rigid layer between the first flexible layer and the lower adhesive layer. A third thin hard layer above the adhesive layer could assist in the manufacturing process and channel creation without affecting the adhesive layer.

A gradation of rigidity within the first layer could also be employed. For example, the upper surface of the first layer and the lower portion of the first layer could be chemically, mechanically, or thermally treated to be relatively firm. A third thin hard layer would not be necessary.

In another embodiment of the invention, a small, firm but pliable substrate or pad comprising the catheter management system can lie on a surgical field, separated from, for example, an introducer sheath, vascular access point, or Y-adaptor. The substrate or pad can be attached to the skin or sterile drapes or some other item in the surgical field to maintain its desired position relative to an introducer sheath, vascular access point, or Y-adaptor. The substrate or pad typically has between one and twelve channels, preferably from two to eight or from four to six, channels on it, adapted to hold in place one to twelve associated flexible elongated medical devices or members, with the associated flexible elongated members typically comprising, for example, a guide wire and a catheter. The flexible elongated medical devices or members are said herein to be "associated" with each other because the guide wire and the catheter are used together. The channels can be arranged in a parallel or a curved layout, so as to "fan out" the wire/catheter pairs and to assist in keeping the free ends of each wire/catheter pair separated from the free ends of other pairs. The channels are designed to allow easy insertion and removal of the flexible elongated medical devices or members. Some of the channels can be designed to securely hold a wire or catheter against axial movement, while others can be designed to simply hold a wire or catheter in place relative to the others, without restricting the axial movement of the wire or catheter being held.

The substrate or pad of the catheter management system has an adhesive surface on its lower side, to allow it to adhere directly to a patient's skin or to a drape or other item to keep it in place on a surgical field, with a selected separation from, and orientation relative to, for example, an introducer sheath, vascular access point, or Y-adaptor. The adhesive surface can be selectively exposed by removing a peel-off cover by pulling off an edge from a protective cover or a tab that extends from said protective cover. It is also within the scope of the invention that instead of an adhesive surface, the bottom portion of the substrate or pad could have VELCRO® hooks, clips, or other functional means to attach the substrate or pad to a desired site on or near a patient.

The substrate or pad can optionally have labels for identifying each wire and each catheter, or each wire/catheter pair. These can be stick-on type labels, or surfaces adapted for writing upon, or they can be pre-molded labeling areas on the pad, with punch-out circles identifying the selected location of each wire/catheter pair.

In another embodiment of the invention, a catheter management system comprises a flexible substrate for organizing and stabilizing electrophysiology catheters and/or implantable pacemaker and/or defibrillator leads (all termed "wires"). Preferably the system can be sterilized, is disposable, and is inexpensive to manufacture.

In another embodiment of the invention, the system comprises an upper malleable surface with one or more parallel linear channels in which the "wires" can be easily depressed and secured to stabilize the position of said "wires" inside the heart and/or circulatory system. In addition, the "wires" can be easily removed from a channel to freely manipulate said "wires."

In another embodiment of the invention, an upper malleable surface may comprise one or two separate layers. If two separate layers are used, the top upper layer is less malleable and firm to keep the wires contained within, and the lower more malleable material is conformable to the shape of the wire and provides resistance to prevent catheter movement.

In another embodiment of the invention, the system has a lower adhesive surface protected by removable tape to secure said system to a sterile drape or surface.

In another embodiment of the invention, there is an additional firm layer placed above the adhesive layer, which would allow the easy manufacturing and placement of slits in the catheter management system. Slits could easily be cut through an upper surface (firm to malleable) but could stop at a thin hard surface above the adhesive tape.

In another embodiment of the invention, there is an additional curved layer placed below a firm layer and placed above or forming part of the adhesive layer, which would facilitate the easy placement of the catheter management system on a curved surface (for example, a patient's thigh) without deforming the slits on the opposite side of the rigid layer.

In another embodiment of the invention, the channels would actually be gaps in which both sides of portions of the upper surfaces do not touch. A space, such as, 20 to 30 mil, may exist to allow easy access an elongated medical device or member into the catheter management system's channels. Without such a gap, it would be more difficult to place elongated medical devices or members directly into the channels. In addition, an additional firm layer provides enough resistance to permit finger pressure over the elongated medical device or member and its entry into the channel. The channel must be wide enough and/or deep enough to receive the catheter, guide wire, sheath, lead, or other elongated medical device or member in whatever shape or size is intended to be received. The sides of the channels may be parallel, or the top of a channel may be wider than the bottom of the channel, or vice versa.

In another embodiment of the invention, the upper surface may not have discrete differences in firmness but rather more gradual differences in firmness.

In another embodiment of the invention, the catheter management system may include a firm component which could be inserted within a sheath and used to slit biventricular pacemaker, regular pacemaker, and/or defibrillator lead introducer sheaths such that the introducer sheaths themselves could be easily removed while channels of said sheath maintain the lead or leads in their position. Alternatively, the catheter management system could maintain all inserted leads in position and allow slitting of their introducer sheaths and removal of said sheaths using the standard built-in sheath removal embodiments.

In another embodiment of the invention, there is a rigid layer between the patient and a flexible channel layer to ensure that a channel used to hold an elongated medical device or member does not open or release with patient movement or curvature of adhesive surface. The rigid layer would have properties which are stiffer or less malleable than the layer with cut channels.

In another embodiment of the invention, there is a flexible layer between two rigid layers to ensure that a channel used to hold an elongated medical device or member does not open or release with patient movement. The rigid layers would have properties which are stiffer or less malleable than the layer with cut channels.

In another embodiment of the invention, the catheter management system comprises a flexible layer to face the patient that is cut or shaped to help minimize the effect of the curved surface to which the catheter management system must adhere. The curved surface would have adhesive on the patient side allowing for the top surface of the catheter management system to remain flat or linear instead of curved during application and preventing the channels from opening and releasing or applying less force to the one or more elongated medical devices or members being held.

In another embodiment of the invention, the catheter management system has advertising/marketable/instruction material printed on the upside of said system to advertise/market and/or instruct/provide additional information during a procedure. Such information is now between the operator and the patient during said procedure.

In another aspect of the invention, there may be two or more catheter management systems arranged, for example, in parallel, about 1 to about 3 feet apart, to manage and separate two or more catheters, guide wires, sheaths, leads, or other elongated medical devices or members.

In another embodiment of the invention, a sterile, sterilizable, or unsterile disposable multilayered device for managing catheters, guide wires, sheaths, leads, or other elongated medical devices or members comprises:

an upper firm layer having upper and lower surfaces;

a middle compressible foam layer having upper and lower surfaces, the upper surface of the middle compressible layer being attached to the lower surface of the upper firm layer; and a lower adhesive layer for securing said device to or near a patient, which lower adhesive layer has an upper surface that is attached to the lower surface of the middle compressible layer, wherein one or more lateral channels extend inwardly from the upper surface of the upper firm layer through the middle compressible layer to the upper surface of the lower adhesive layer, and wherein one or more catheters, guide wires, leads, sheaths, or other elongated medical devices or members can be positioned in the channels to maintain position relative to each other and then easily be removed.

In another embodiment of the invention, a disposable multilayered device for organizing, holding, and releasing elongated medical devices or members such as catheters, wires, leads, and/or sheaths comprises:

an upper firm layer having upper and lower surfaces;

a middle compressible foam layer having upper and lower surfaces, the upper surface of the middle compressible layer being attached to the lower surface of the upper firm layer;

a lower firm layer to provide resistance when pushing an elongated member into said device to secure it; and a lower patient contact adhesive layer for securing said device to or near a patient, which adhesive layer has an upper surface that is attached to the lower surface of the lower firm layer, wherein one or more lateral channels extend from the upper surface of the upper firm layer through the middle compressible layer to the lower firm layer, and wherein one or more elongated medical devices or members can be positioned in the channels to maintain position and then easily be removed.

In another embodiment of the invention, an elongated medical device or member is secured by pushing down on both sides of the channels and releasing. Removal is achieved by pulling up on the elongated medical device or member.

In another embodiment of the invention, an elongated medical device or member is secured in place by pushing down on the groove and pulling up to release the elongated medical device or member.

In another embodiment of the invention, the channels are substantially parallel to each other.

In another embodiment of the invention, the channels form a fan configuration as viewed from above.

In another embodiment of the invention, the device comprises a firm layer between the middle compressible layer and the lower adhesive layer.

In another embodiment of the invention, the upper surface of the upper firm layer is capable of displaying indicia.

In another embodiment of the invention, the lateral channels may be the same size or variable in size to accommodate a variety of elongated medical devices or members of different widths.

In another embodiment of the invention, two or more catheter management systems are organized adjacent to one another (and separated by a comfortable working distance of from about 0.5 to about 6 inches) but perpendicular to the elongated medical devices or members to organize the elongated members and/or their connector cables and prevent entanglement of said members.

In another embodiment of the invention, two or more catheter management systems are organized parallel to one another (and separated by from about 0.5 to about 3 feet) but perpendicular to the elongated medical devices or members to organize the elongated medical devices or members and/or their connector cables and prevent entanglement of said members.

In another embodiment of the invention, a labeling system is also provided to help identify each elongated medical device or member.

In another embodiment of the invention, a disposable multilayered device for managing elongated medical devices or members comprises:

an upper component having upper and lower surfaces, wherein one or more lateral channels extend from the upper surface of the upper component into the upper component; and a lower component capable of releasably attaching to a desired location on or near a patient, wherein one or more elongated medical devices or members can be positioned in the channels to maintain position relative to each other and then easily be removed.

In another embodiment of the invention, a sterile, sterilizable, or unsterile disposable multilayered device for managing elongated medical devices or members comprises:

a first layer having upper and lower surfaces and having one or more lateral channels extending therethrough;

a second layer positioned beneath the first layer and having upper and lower surfaces;

a third, firm layer having a top surfaced affixed to the lower surface of the second layer and a lower surface; and a fourth layer having an upper surface attached to the lower surface of the third layer and a lower adhesive surface for securing said device to or near a patient, wherein the upper layer of the first layer is firmer than the rest of the first layer, and wherein one or more elongated medical devices or members can be positioned in the channels to maintain position relative to each other and then easily be removed.

In another embodiment of the invention, the first layer and the second layer are together a continuous component.

In another embodiment of the invention, a catheter management system is fabricated in a manner as to create a structure with a variety of layers of different quantifiable properties related to hardness, bendable, flexibility, tensile strength, and/or stress and strain. The combination of these properties creates a system in which at least one elongated member and/or medical device can be pushed into a channel, slot, slit, or gap such that the system contains at least one layer that is more flexible to absorb, conform to, and grip said medical device and/or elongated member and another layer that is less flexible (i.e., harder) to provide resistance when pushing the at least one medical device and/or elongated member into the slit, slot, channel, or gap of the catheter management system. This embodiment also would have an attached bottom layer such that the catheter management system could easily adhere or attach to a patient, sterile drape, and/or other support system or table on or around a patient.

In another embodiment of the invention, at least one of the layers is comprised of an upper continuous component, with the addition of an adhesive layer or structure on the bottom. The upper continuous component is formed by a process, which creates a single biomaterial a continuous component identifiable by a variety of stress and strain properties, flexibility, resilience, hardness, or any other characteristic determining the ability of said structure to bend, or move under a force. Said continuous component could be comprised of a polymer, copolymer, plastic or rubber, thermoplastic, composite material, admixture, polymeric matrix, crystalline structure, polyethylene/polyacetate/-polycarbone/polychloroprene/glass/carbon/graphite/silicone/boron/ceramic/organic fibers or combination thereof. It is also understood that the continuous component could be fabricated in a variety of manners.

The novel features of this invention, as well as the invention itself, will be best understood from the attached

DETAILED DESCRIPTION OF THE INVENTION

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. It should be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1:
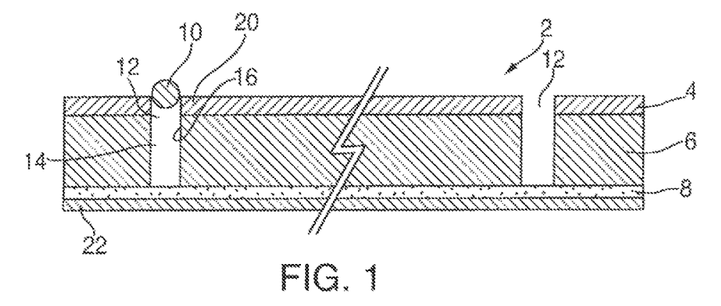
FIG. 1 is a schematic cross-sectional representation of an embodiment of the invention.

As shown in FIG. 1, a section 2 of a catheter management system according to the invention comprises a firmer upper surface or layer 4, a less firm middle layer 6, and a non-allergenic adhesive layer 8 comprising a substrate. A "wire" 10, such as a catheter, guide wire, lead, sheath, or other elongated medical device or member, is positioned at the opening or entrance 12 to a lateral groove, slit, slot, gap, or other opening, i.e., channel, 14 having inner surfaces 16. When the operator (not shown) presses downward on wire 12, upper surface sections 20 of layer 4 bend downward so that the middle layer 6 on each side of channel 14 is compressed. Then, wire 10 moves downward below sections 20, sections 20 recoil upward, and inner surfaces 16 compress wire 10, trapping wire 10. Surfaces 16 and middle layer 6 provide resistance, that is, they prevent movement while upper layer 4 holds wire 10 in. Catheter management system 2 as well as the other embodiments shown and described herein will preferably have a removable polymeric layer 22 covering the bottom of adhesive layer 8.

Figure 2:
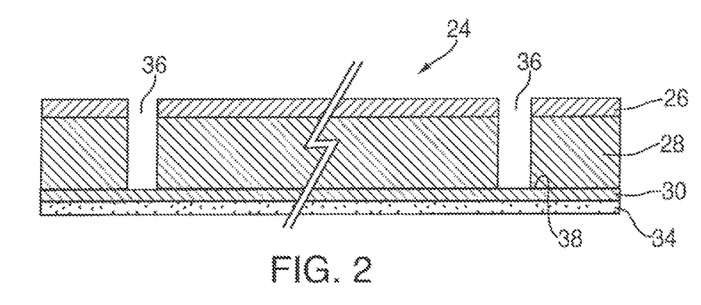
FIG. 2 is a schematic cross-sectional representation of another embodiment of the invention.

Removal of wire 10 is easy. From the side the operator applies upward pressure to wire 10 so that it is pushed up from section 2 and released for manipulation In the embodiment of the invention shown in FIG. 2, a catheter management system 24 comprises a firmer upper surface or layer 26, a less firm middle layer 28, a lower layer 30, and a non-allergenic adhesive layer 34. Lateral grooves, slits, slots, or gaps or other openings, i.e., channels, 36 extend from upper layer 26 to the upper surface 38 of lower layer 30.

Figure 3:
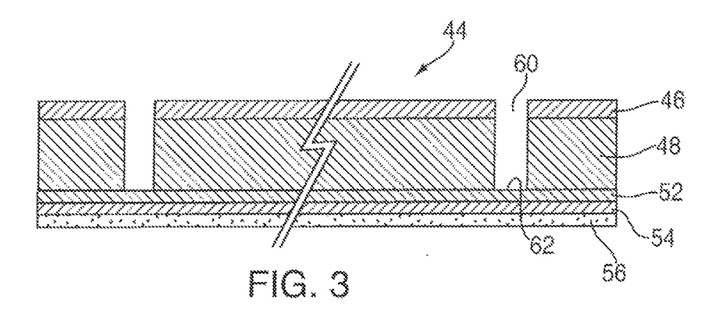
FIG. 3 is a schematic cross-sectional representation of a further embodiment of the invention.

In the embodiment of the invention shown in FIG. 3, a catheter management system 44 comprises a firmer upper layer or surface 46, a less firm middle layer 48, a rigid layer 52, optionally a lower layer 54, and an adhesive layer 56. Lateral grooves, slits, slots, gaps, or other openings, i.e., channels, 60 extend from upper layer 46 to an upper surface 62 of rigid layer 52.

Figure 4:
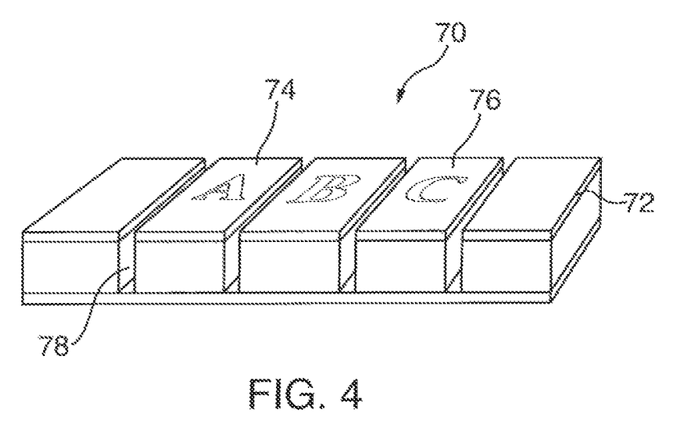
FIG. 4 is a schematic oblique representation of an embodiment of the invention.

In FIG. 4, a catheter management system 70 has an upper layer 72 with an upper surface 74 upon which printing or other indicia 76, such as instructions, a warning, or a company name or logo, or any combination thereof could appear. Whereas the grooves, slits, slots, gaps, or other openings, i.e., channels, 78 might normally be spaced uniformly across upper surface 74, optionally channels 78 may be positioned so that there is a larger upper surface for such indicia. Also, two or more of channels 78 may be parallel or non-parallel. For example, channels 78 may be arranged in a fan shape.

Figure 5:
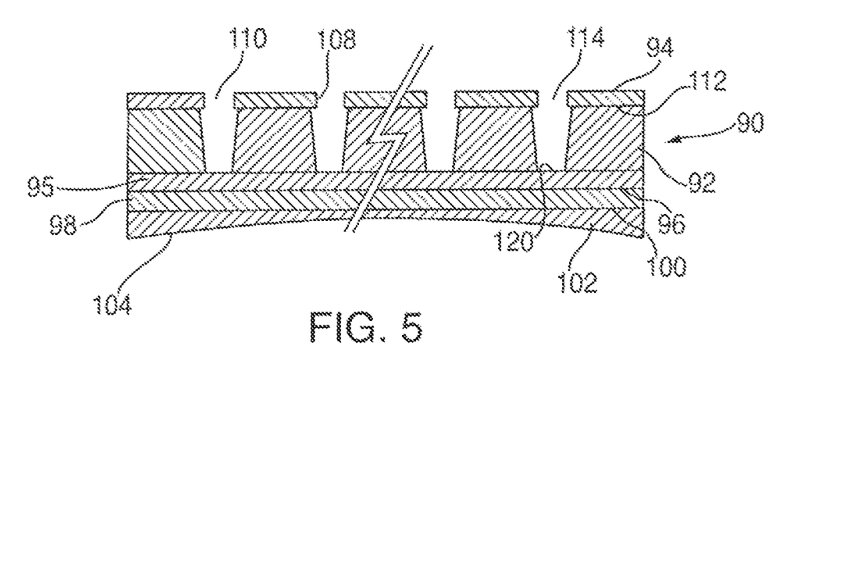
FIGS. 5 and 6 are each a schematic cross-sectional representation of another embodiment of the invention.
Figure 6:
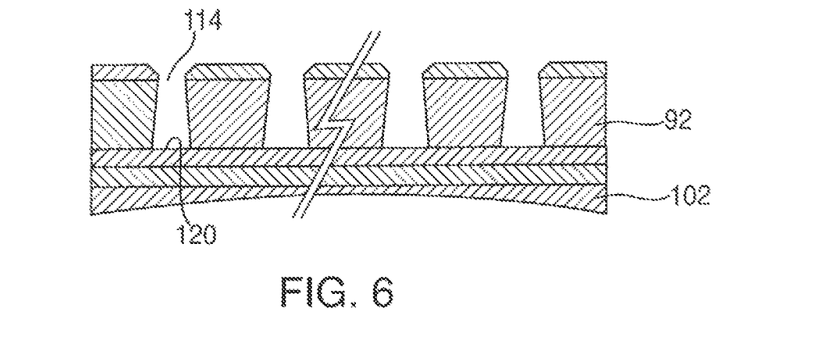

The catheter management systems set forth in FIGS. 5 and 6 represent additional embodiments of the invention. In FIG. 5, a system 90 has a first layer 92 with an attached upper layer or surface 94 comprised of material firmer than the material of first layer 92. First layer 92 is attached to second layer 95, which is in turn attached at boundary 96 to a firmer third layer 98. The lower surface of third layer 98 is attached at boundary 100 to a fourth, adhesive layer 102. Adhesive layer 102 has a surface 104, preferably curved, that comprises adhesive or other chemical or mechanical means for bonding with a patient's skin or clothing or with a drape or other flexible or hard surface in an operating room or medical facility (not shown).

Upper layer or surface 94 can be coextensive with the upper boundary 112 of first layer 92 or the lateral edges 108 of upper layer or surface 94 can extend into a channel 110 as shown in FIG. 5 or be withdrawn or recessed from channel 110 as shown in FIG. 6.

As can be seen, channel 110 can be wider at its top 114 than at its bottom 120, as in FIG. 5, or narrower at its top 114 than at its bottom 120, as in FIG. 6. Optionally, as shown in other embodiments, the sides of channel 110 can be substantially parallel.

Although first layer 92 and second layer 95 are depicted as two separate components, it is within the scope of the invention that first layer 92 and second layer 95 can form a single continuous unit, element, or component of the same material.

Overall the catheter management system of the invention comprises firm but flexible material. Upper layers 4, 26, 46, 72, and 94 and rigid layers 52 and 98 comprise a rigid or semi-rigid polymeric material such as a polycarbonate. Useful polymeric materials include, but are not limited to, LEXAN® polycarbonate materials available from GE Plastics.

Middle layers 6, 28, 48, and 95 comprise a less rigid, more resilient polymeric material such as a polyacetate, polycarbonate, or polyethylene foam. Useful polymeric foams include, but are not limited to, ethylene vinyl acetate and many of the polychloroprene synthetic rubbers available as Neoprene from DuPont. Lower layers 30 and 54 preferably comprise a polymeric material that is less resilient than the middle layer, such as a polycarbonate. Useful polymeric materials for this layer include, but are not limited to, LEXAN® polycarbonate materials.

Adhesive layers 8, 34, 56, and 102 comprise pre-formed adhesive tape that is sticky on both the upper and lower surfaces and has peel away protective tape on both surfaces. One surface is exposed when the catheter management system is assembled; the other surface is exposed when the catheter management system is applied to a desired surface. Examples of adhesive tapes or substrates that are useful include 3M's 1587 and 1772 contact adhesives, which have a 1/16" polyethylene foam substrate. Alternatively, direct adhesive could be applied to the bottom surface with protective peel off tape with a tab to provide easy removal.

Individual layers are bound together by an appropriate medical grade adhesive. 3M's 1510 acrylic adhesive has been useful in this regard. In addition, individual layers can be adhered together by heat or other chemical or mechanical means.

Optionally the catheter management system could have two or more flat tabs to provide surfaces to which surgical clamps can be attached, to hold the pad, for example, on a surgical drape. In addition, the bottom adherent surface could be a VELCRO® component or clip.

With regard to grooves, slots, gaps, slits, or other openings in the upper surface of the catheter management system, a groove, slot, gap, slit, or other opening can be pushed open, and a catheter, guide wire, sheath, lead, or other elongated medical device or member can be inserted laterally into the groove, slot, gap, slit, or other opening, which will then close back around the catheter, guide wire, sheath, lead, or other elongated medical device or member and hold it in place, to prevent movement in the transverse or axial direction.

The depths of the various layers can vary according to the application and materials. Typically the upper layers 4, 26, 46, 72, and 94 will each be from about 0.3 mm to about 0.7 mm thick, and the middle layers 6, 28, 48, and 92 will each be from about 0.1 cm to about 0.5 cm thick. Lower layers 30, 54, and 95 will each be from about 0.1 cm to about 0.3 cm thick, and adhesive layers 8, 34, 56, and 102 will each be about 0.1 cm to about 2.5 cm thick. Channels 14, 36, 60, and 110 can be from about 0 mils (a slit) to about 30 mils wide, preferably from about 20 to about 30 mils wide (what are termed gaps). Channels 14, 36, 60, and 110 are preferably from about 1.5 cm to about 2.0 cm apart, but this can vary, according to the operator's wishes, habits, or desires. Additional sizes and dimensions could be configured for microsurgical applications as well as macrosurgery.

The grooves, slits, slots, gaps, or openings can vary in shape and size to accommodate catheters, guide wires, leads, sheaths, or other medical devices or members, which have different diameters. However, thin slits in the above design can accommodate a variety of elongated medical device or member sizes and shapes due to the material engineering design (firm but malleable upper layer and softer lower layer or some variation thereof).

The dimensions of the catheter management system can vary greatly due to the intended application and the number of "wires" that may be used. In one embodiment of the invention, the substrate may have a length of from about 0.5 to about 10.0 inches, a width of from about 0.2 to about 5.0 inches, and a thickness of from about 0.1 to about 0.5 inches.

It is within the scope of the invention that a catheter management system, that is, a sterile disposable multilayered device for managing catheters, guide wires, leads, sheaths, or other medical devices, can be more simply viewed as a two component system. As a first component, an upper component has upper and lower surfaces, wherein one or more lateral grooves, slots, or gaps extend from the upper surface of the upper component into the upper component. The second component comprises means of, attaching, optionally releasably attaching, to a desired location on or near a patient. One or more catheters, guide wires, leads, sheaths, or other medical devices or members can be positioned in the grooves, slots, or gaps to maintain position relative to each other and then easily be removed.

The first component may comprise the one or more layers described above, where the first component may have firm, soft, and then firm layers, or firm, soft, soft, and firm layers. Moreover, whereas there may two adjacent layers that could be the same material, there may in fact only be one layer, for example, one where the gaps, grooves, or slots do not go through the entire combined layer but only to a depth consistent with what may have been the first upper layer.

In one embodiment of the invention, the catheter management system may comprise predetermined sizes of perhaps about 4 to about 12 inches in length. Optionally the catheter management system may comprise longer lengths that can be cut to size, dependent upon the number of expected elongated medical devices or members. Alternatively, the catheter management system could be perforated or otherwise frangible at regular or irregular intervals so that lengths of useful size can be cut or torn off.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. A disposable multilayered device for releasably holding elongated medical devices or members on or near a patient, which consists essentially of:
   an upper firm layer having upper and lower surfaces;
   a middle compressible foam layer having upper and lower surfaces, the upper surface of the middle compressible foam layer adhering to the lower surface of the upper firm layer; and
   a lower adhesive layer having upper and lower surfaces, for securing said device to or near the patient, wherein the upper surface of the lower adhesive layer adheres to the lower surface of the middle compressible foam layer,
   wherein the device has a first longitudinal lateral surface and a second, oppositely positioned longitudinal lateral surface,
   wherein one or more laterally extending channels extend horizontally from the first longitudinal lateral surface to the second longitudinal lateral surface and vertically from the upper surface of the upper firm layer through the middle compressible foam layer to the upper surface of the lower adhesive layer, and
   wherein one or more elongated medical devices or members can be positioned in the laterally extending channels to maintain position relative to the disposable multilayered device and then be easily removed.

2. The device of claim 1 wherein the elongated medical device or member is secured by pushing down on both sides of the upper surface of the upper firm layer adjacent the one or more laterally extending channels and then releasing, and the elongated medical device or member is removed by pulling up on the elongated medical device or member.

3. The device of claim 1, wherein the elongated medical device or member is secured in place by pushing down on the elongated medical device or member positioned over the one or more laterally extending channels in the upper surface of the upper firm layer, and the elongated medical device or member is removed by pulling up to release it.

4. The device of claim 1, wherein the laterally extending channels are substantially parallel to each other.

5. The device of claim 1, wherein the upper surface of the upper film layer is capable of displaying indicia.

6. The device of claim 1, wherein the laterally extending channels may be the same size or variable in size to accommodate a variety of the elongated medical devices or members of different widths.

7. An assembly of two or more devices of claim 1, wherein more than one device is organized parallel to one another, and separated but perpendicular to the elongated medical devices or members to organize the elongated medical devices or members or their connector cables and prevent entanglement of said elongated medical devices or members.

8. The device of claim 1, wherein a labeling system is also provided to help identify each elongated medical device or member of the one or more elongated medical devices or members.

9. The device of claim 1, wherein the elongated medical devices or members are selected from the group consisting of catheters, guide wires, leads, and sheaths.

10. The device of claim 1, wherein the adhesive layer is curved to configure to a patient's body or a curved substrate.

11. The device of claim 10, which mitigates the natural bend of the device when the device is placed on a smooth surface.

12. A disposable multilayered device for releasably holding elongated medical devices or members on or near a patient, which consists essentially of:

an upper firm layer having upper and lower surfaces;

a middle compressible foam layer having upper and lower surfaces, the upper surface of the middle compressible foam layer adhering to the lower surface of the upper firm layer;

a lower firm layer having upper and lower surfaces, wherein the upper surface of the lower firm layer adheres to the lower surface of the middle compressible foam layer and the lower firm layer provides resistance when one or more elongated medical devices or members is pushed vertically into a laterally extending channel of the device to secure the elongated medical device or member; and a lower adhesive layer having upper and lower surfaces, for securing said device to or near the patient, wherein the upper surface of the lower adhesive layer adheres to the lower surface of the lower film layer, wherein the device has a first longitudinal lateral surface and a second, oppositely positioned longitudinal lateral surface, wherein one or more laterally extending channels extend horizontally from the first longitudinal lateral surface to the second longitudinal lateral surface and vertically from the upper surface of the upper firm layer through the middle compressible foam layer to the upper surface of the lower firm layer, and wherein the one or more elongated medical devices or members can be positioned in the laterally extending channels to maintain position relative to the disposable multilayered device and then be easily removed.

* * * * *